US010426365B1

(12) United States Patent
Parhi et al.

(10) Patent No.: US 10,426,365 B1
(45) Date of Patent: Oct. 1, 2019

(54) METHOD AND APPARATUS FOR PREDICTION AND DETECTION OF SEIZURE ACTIVITY

(71) Applicant: Keshab K Parhi, Maple Grove, MN (US)

(72) Inventors: Keshab K Parhi, Maple Grove, MN (US); Zisheng Zhang, St. Paul, MN (US)

(*) Notice: Subject to any disclaimer, the term of this patent is extended or adjusted under 35 U.S.C. 154(b) by 475 days.

(21) Appl. No.: 14/121,426

(22) Filed: Sep. 5, 2014

Related U.S. Application Data

(60) Provisional application No. 61/959,692, filed on Aug. 30, 2013.

(51) Int. Cl.
| | |
|---|---|
| *A61B 5/00* | (2006.01) |
| *A61B 5/04* | (2006.01) |
| *A61B 5/048* | (2006.01) |

(52) U.S. Cl.
CPC .......... *A61B 5/04014* (2013.01); *A61B 5/048* (2013.01); *A61B 5/4094* (2013.01); *A61B 5/4836* (2013.01); *A61B 5/7257* (2013.01); *A61B 5/7267* (2013.01)

(58) Field of Classification Search
CPC . A61B 5/04012; A61B 5/04014; A61B 5/048; A61B 5/4094; A61B 5/7257; A61B 5/7267
USPC .............................. 600/544; 706/15, 22, 45
See application file for complete search history.

(56) References Cited

U.S. PATENT DOCUMENTS

| | | | | |
|---|---|---|---|---|
| 5,995,868 | A * | 11/1999 | Dorfmeister | A61B 5/048 600/300 |
| 8,005,534 | B2 * | 8/2011 | Greenwald | A61B 5/048 600/544 |
| 2003/0195602 | A1 * | 10/2003 | Boling | A61N 1/05 607/122 |
| 2005/0216071 | A1 * | 9/2005 | Devlin | A61B 5/0476 607/48 |
| 2005/0267362 | A1 * | 12/2005 | Mietus | A61B 5/0205 600/429 |
| 2006/0265022 | A1 * | 11/2006 | John | A61B 5/4094 607/45 |
| 2011/0224528 | A1 * | 9/2011 | Choi | A61B 5/0478 600/383 |

(Continued)

OTHER PUBLICATIONS

Bandarabadi et al., Epileptic seizure prediction using relative spectral power features, Clinical Neurophysiology, vol. 126, pp. 237-248, Jun. 4, 2014.

*Primary Examiner* — Kristen Matter
(74) *Attorney, Agent, or Firm* — Westman, Champlin & Koehler, P.A.; Theodore M. Magee

(57) ABSTRACT

The present invention relates to the design and implementation of a seizure detection or prediction system. The proposed invention computes and selects spectral power ratio features, cross-channel spectral power ratio features, cross spectral power features and cross spectral power ratio features in a patient-specific manner. The selected features are input to a classifier to detect or predict seizures. The proposed algorithm takes advantage of high sensitivity in detecting or predicting seizures and low complexity in implementation. The proposed scheme is general and is suitable for creating a trigger for therapy delivery in a closed-loop therapy system. The therapy could involve either delivery of an anti-epileptic drug or electrical or magnetic stimulation of the brain.

11 Claims, 28 Drawing Sheets

(56) References Cited

U.S. PATENT DOCUMENTS

| | | | | |
|---|---|---|---|---|
| 2011/0245707 | A1* | 10/2011 | Castle | A61B 5/4094 |
| | | | | 600/544 |
| 2013/0274625 | A1* | 10/2013 | Sarma, Sr. | A61B 5/048 |
| | | | | 600/544 |
| 2015/0227702 | A1* | 8/2015 | Krishna | G06F 19/345 |
| | | | | 705/2 |

* cited by examiner

Prior Work

Fig. 2: Prior Work

Prior Work

METHOD AND APPARATUS FOR PREDICTION AND DETECTION OF SEIZURE ACTIVITY

FIELD OF THE INVENTION

Certain embodiments of the invention relate to processing of Electroencephalogram (EEG) signals to predict and detect seizures in epileptic patients. More specifically, certain embodiments of the invention relate to methods and devices for predicting and detecting seizures by using patient-specific features such as ratios of spectral power in different bands of an electrode or two bands of two different electrodes. Other features proposed include cross spectral power density features such as ratio of cross spectral power between bands of two different channels or cross spectral power density in a specific band.

BACKGROUND OF THE INVENTION

Approximately 1% of the world's population suffers from epilepsy which is the second most common neurological disorder and is characterized by seizures. Reliable seizure detection and prediction are therefore important for not only improving the lives of epileptic patients, but also in assisting the epileptologists in marking seizures in the electroencephalogram (EEG) recordings. An apparatus that can detect or predict seizures can be used in a closed-loop therapy system to deliver an anti-epileptic drug or other therapy, such as neurostimulation, as needed.

Therefore, there is a current need for designing algorithms for a wearable or an implantable device that can reliably detect or predict seizures with low computational complexity. In particular, the algorithm should require low power consumption and low hardware cost when implemented in an apparatus that can detect or predict seizures.

BRIEF SUMMARY OF THE INVENTION

Methods for designing a system architecture that is able to reliably detect or predict seizures are provided. The invention is suited for low-power biomedical monitoring systems for detecting or predicting seizures. In one embodiment of the invention, such an apparatus can trigger delivery of anti-epileptic drugs or other therapy. In another embodiment of the invention, the system can be used to mark seizures in unmarked EEG recordings.

The present invention proposes new algorithms and system architectures for seizure detection or prediction. In one embodiment, the algorithm can be applied to a single EEG channel. In another embodiment, the algorithm can be applied to a plurality of channels. The EEG signals could be collected as a monopolar EEG signal from one electrode or as a bipolar signal as the difference of two monopolar signals.

This algorithm can be coded in a computer language and then be executed by any computing device. The system architecture can also be implemented using digital circuits in a wearable or implantable device.

The seizure detection or prediction method uses a single-channel or multi-channel EEG data collected from a subject's brain. The EEG recording could be a scalp recording or an intracranial recording. Other types of signals from the brain such as local field potentials may also be used. In prior art, features have been extracted from the windowed EEG signal such as power spectral densities (PSD) in various bands from one or more electrodes. In a EEG signal processing system, typical bands include (1) $\theta$ (3-8 Hz), (2) $\alpha$ (8-13 Hz), (3) $\beta$ (13-30 Hz), (4) $\gamma$ (30-128 Hz). In another embodiment, the $\gamma$ band is further split into 5 sub-bands: (1) $\gamma1$ (30-47 Hz), (2) $\gamma2$ (53-70 Hz), (3) $\gamma3$ (70-90 Hz), (4) $\gamma4$ (90-97, 103-110 Hz), (5) $\gamma5$ (110-128 Hz). Use of ratio of spectral power in two different bands from one electrode or use of ratio of spectral power in two bands from two different electrodes as a feature to discriminate seizure detection or prediction from interictal state is a key aspect of the proposed invention. Use of ratio of spectral power in two bands from the cross spectral density (CPSD) of two electrodes is another key aspect of the proposed invention. Use of a specific band power from the cross spectral density of two electrodes is also another aspect of the proposed invention.

In one embodiment, features can then be subjected to a postprocessing step to remove undesired noise and fluctuations. Such a postprocessing could be carried out by a moving-average filter or a median filter or a Kalman filter. These denoised features can be input to a classifier to compute a decision variable. In another embodiment, the features could be input to a classifier and the decision variable could be subjected to the said postprocessing step.

Denoised features are then subjected to a feature selection step. In the propose invention, the features are selected in a patient-specific manner such that different patients may use different features for seizure detection or prediction. Another aspect of this invention is that the proposed algorithm selects only a few features from a few electrodes while achieving a high detection or prediction sensitivity and low false detection or prediction rate.

The final step is to identify the signals preceding or during a seizure using univariate or multi-variate classifiers based on the said features. The classifier processes the features and computes a decision variable that is thresholded to classify and detect or predict seizures.

BRIEF DESCRIPTION OF THE DRAWINGS/FIGURES

The present invention is described with reference to the accompanying figures. The accompanying figures, which are incorporated herein, form part of the specification, illustrate the present invention, and together with the description further serve to explain the principles of the invention and to enable a person skilled in the relevant art to make and use the invention.

DETAILED DESCRIPTION OF THE INVENTION

Seizure detection and prediction have been of great interest in past decades. Various algorithms have been proposed to reliably detect or predict the seizures with reduced computational complexity.

Figure 1:
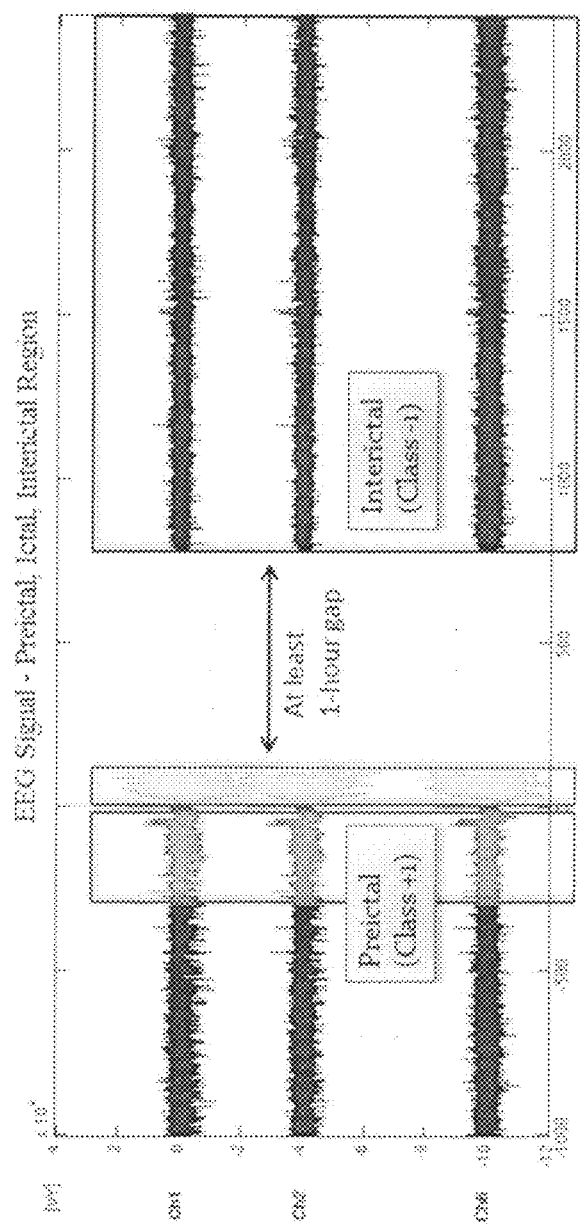
FIG. 1 illustrates multiple raw EEG signals in preictal, ictal and interictal time periods.

A seizure detection (or prediction) problem can be viewed as a binary classification problem, where one class consists of ictal signals corresponding to an occurrence of the seizure (or preictal signal preceding an occurrence of the seizure), and the other class consists of normal EEG signals, also referred as interictal signals. FIG. 1 shows recordings of EEG signals from 6 channels during interictal (baseline), preictal (just before a seizure) and ictal (during seizure) period. The goal of seizure detection is to classify parts of the EEG signal as interictal or ictal, while the goal of seizure prediction is to classify parts of the EEG signal as interictal or preictal.

Figure 2:
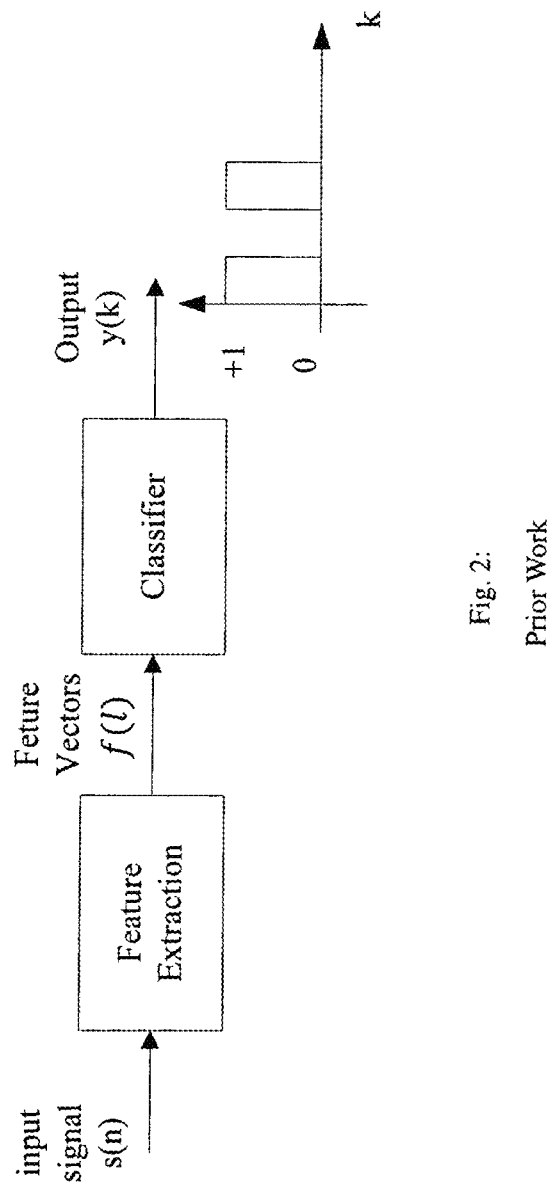
FIG. 2 illustrates the block diagram of a basic seizure detection or prediction algorithm.

A system architecture for any binary classification is shown in FIG. 2. The seizure detection or prediction system also contains 2 parts: (1) feature extraction and (2) classification. Feature extraction step computes discriminating features for the classifier from a single-channel or multi-channel EEG signals. If the features are selected properly such that the between-class distance is large and within-class features are clustered closely, then the classifier will achieve high sensitivity and specificity.

Figure 3:
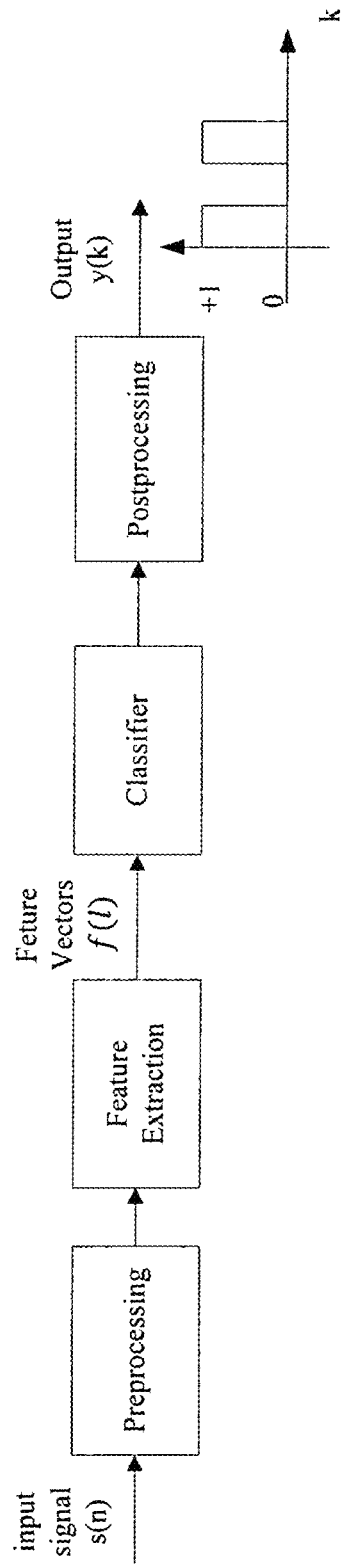
FIG. 3 illustrates the block diagram of an advanced seizure detection or prediction algorithm.

Many seizure detection or prediction methods have been proposed based on the system architecture shown in FIG. 2. In order to enhance the detection or prediction performance, the systems are modified to include preprocessing the input signal before the features are extracted and post-processing the output of the classifier before the final decision is made. This is described by the system architecture shown in FIG. 3.

The proposed seizure prediction algorithm has been tested on the Freiburg and MIT Physionet databases. The intracanial EEG data in the Freiburg dataset were obtained using a Neurofile NT digital video EEG system with 128 channels, 256 Hz sampling rate except Patient 12 whose EEG has been sampled at 512 Hz, and a 16-bit analog-to-digital converter. The Freiburg database contains six contacts of all implanted grid, strip, or depth electrodes: three near the seizure focus (focal) and the other three distal to the focus (afocal). The Freiburg database contains electrocorticogram (ECoG) or EEG from 21 patients suffering from medically intractable focal epilepsy. The amount of available data consists of at least 24 hours of interictal recordings for 21 patients with 2~6 seizures and 50 minutes of preictal data. Seizure onset times and artifacts were identified by certified epileptologists.

The MIT Physionet database, collected at the Children's Hospital Boston, consists of scalp EEG recordings from pediatric subjects with intractable seizures. The International 10-20 system of EEG electrode positions and nomenclature were used for these recordings. Recordings are grouped into 23 cases. Each data contains between 9 and 42 hours' continuous recordings from a single subject. In order to protect the privacy of the subjects, all protected health information (PHI) in the original files have been replaced with bipolar signals (one channel minus another). All signals were sampled at 256 samples per second with a 16-bit resolution. Most files contain 23 single-channel EEG signals.

Intracranial EEG signals from two naturally epileptic dogs are also considered from the Upenn-Mayo Clinic Seizure detection challenge hosted by Kaggle. These signals are sampled at 400 Hz and contains signals from 16 intracranial electrodes.

Figure 4:
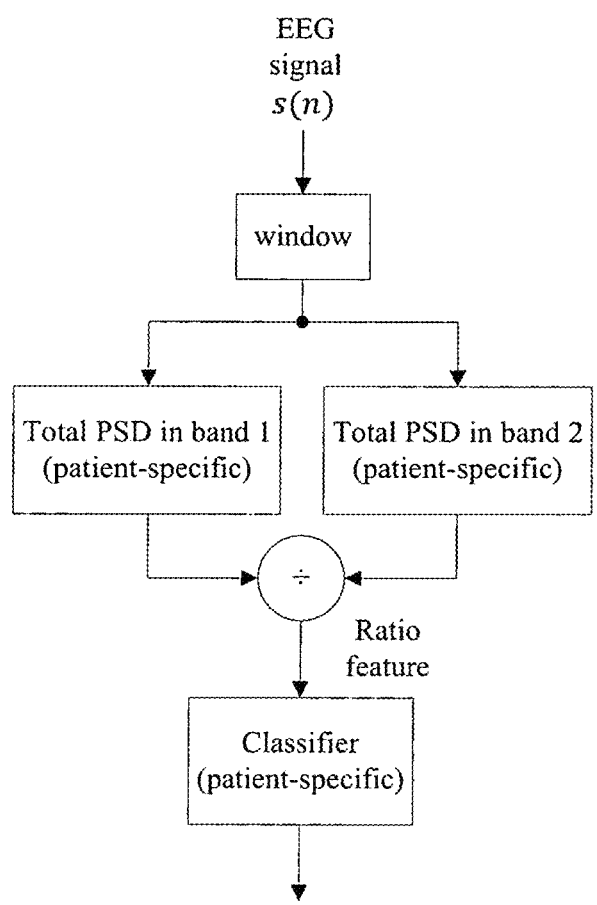
FIG. 4 illustrates the block diagram of the proposed seizure detection or prediction algorithm using a spectral power ratio in two bands computed from a single electrode.
Figure 5:
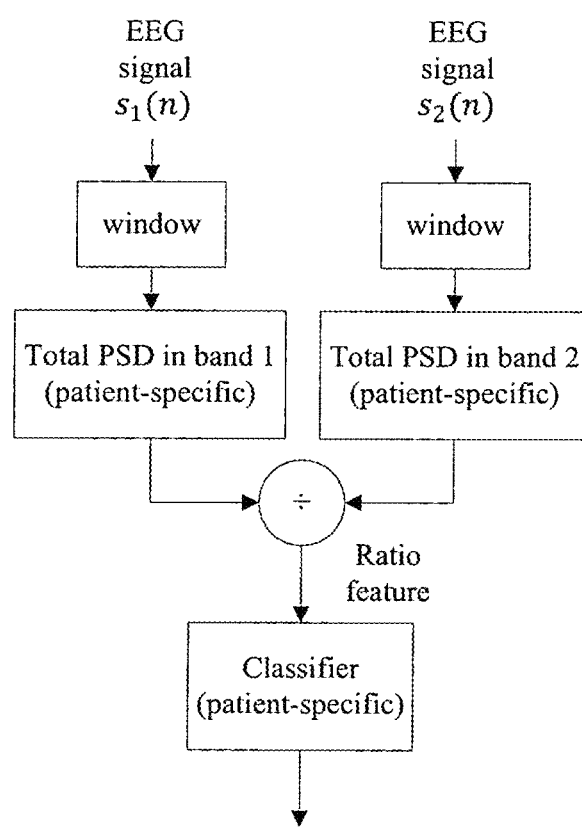
FIG. 5 illustrates the block diagram of the proposed seizure detection or prediction algorithm using a spectral power ratio in two bands computed from two different electrodes.
Figure 6:
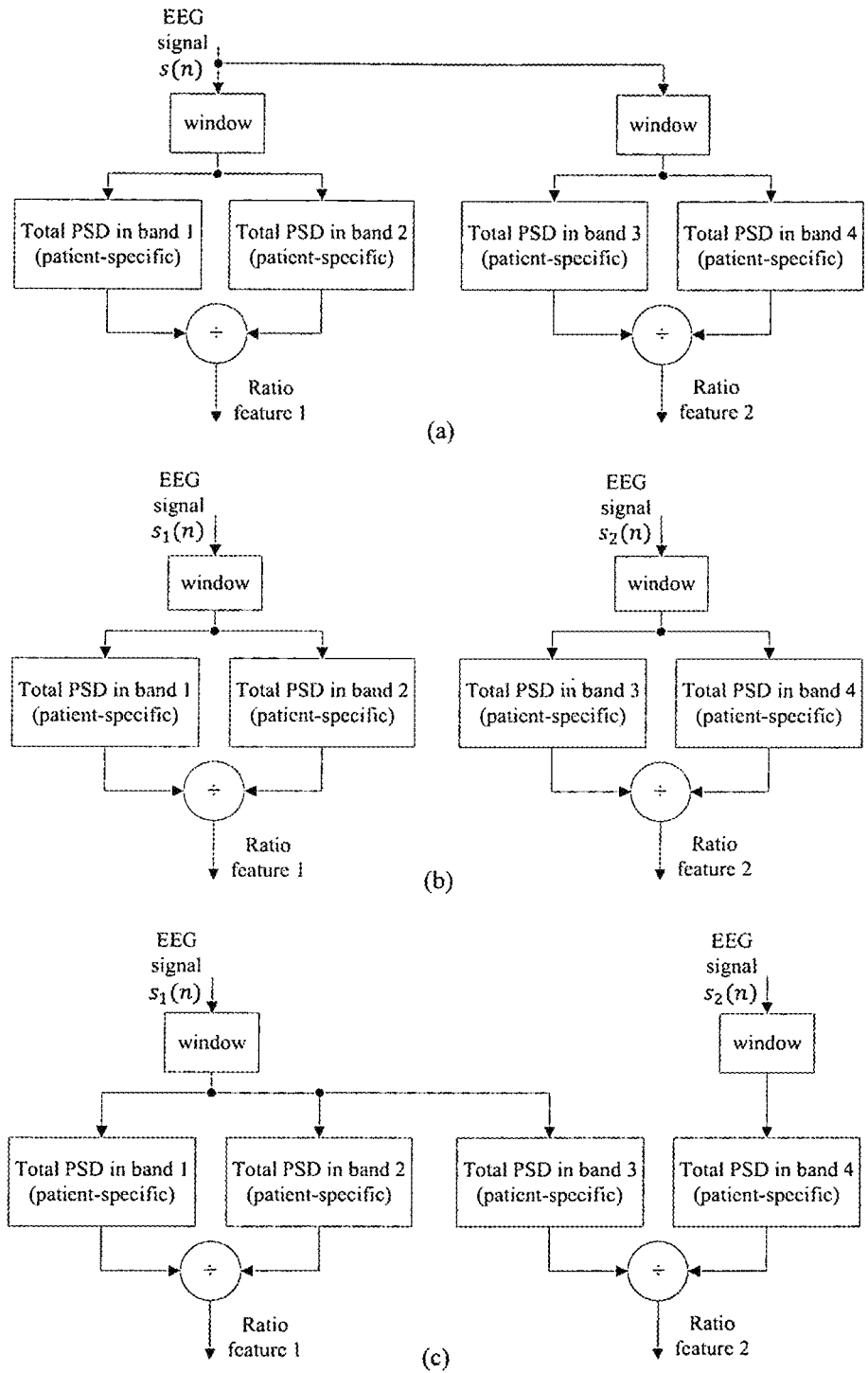
FIG. 6 illustrates various embodiments of the proposed seizure detection or prediction algorithm using (a) multiple spectral power ratios from a single electrode, (b) multiple spectral power ratios from multiple electrodes and (c) spectral power ratio from a single electrode combined with ratio of spectral power in two bands from two electrodes.

This invention presents seizure detection or prediction methods using new features that require less hardware complexity and power consumption. One aspect of this invention is that spectral power ratio features can be used for seizure detection or prediction, as illustrated in FIG. 4, where the two spectral power values of the two bands are computed from the same electrode. In another aspect of the invention shown in FIG. 5, ratio of spectral powers in two bands from two electrodes can be used. FIG. 6 illustrates various embodiments of the proposed seizure detection or prediction algorithm using (a) multiple spectral ratios from a single electrode, (b) multiple spectral power ratios from multiple electrodes and (c) spectral power ratio from a single electrode combined with ratio of spectral power in two bands from two electrodes.

Figure 7:
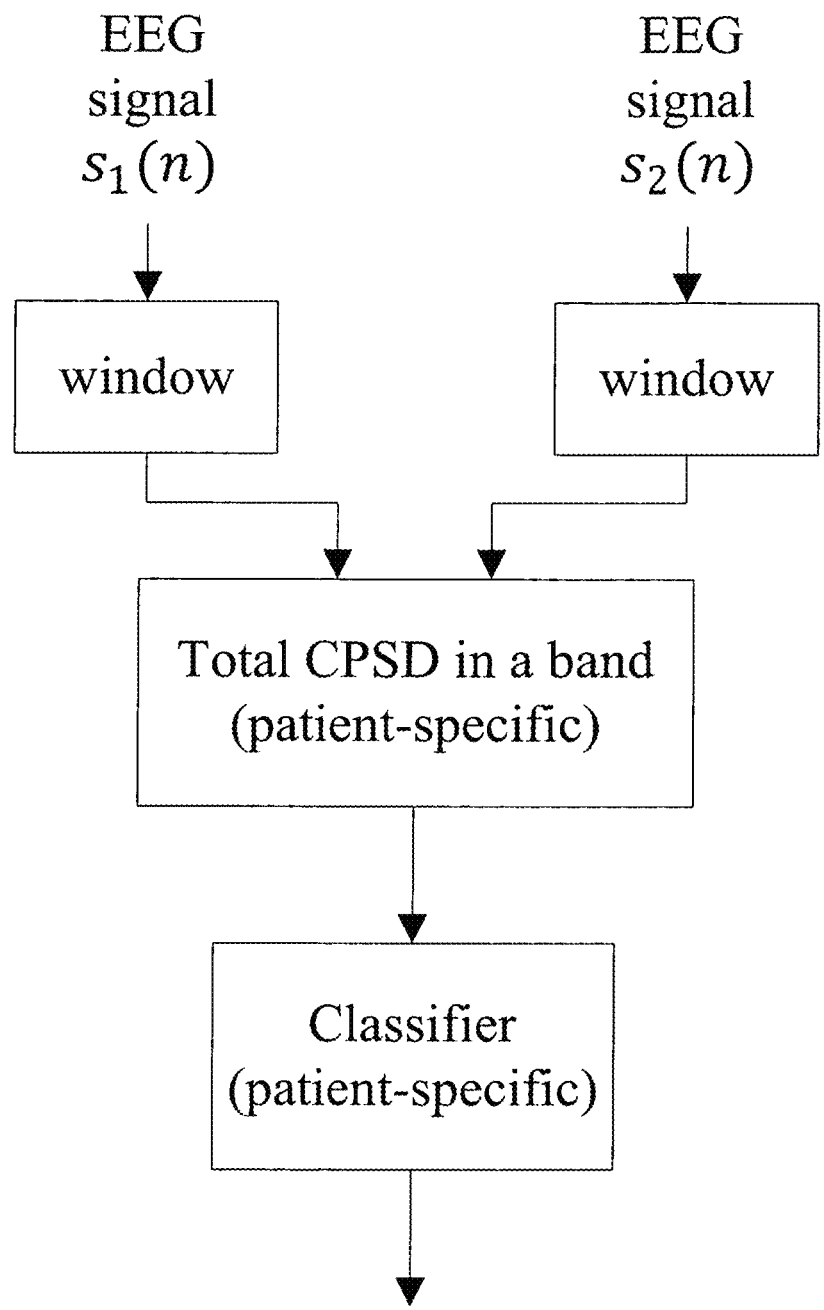
FIG. 7 illustrates the block diagram of the proposed seizure detection or prediction algorithm using a band power in a specific band of the CPSD.
Figure 8:
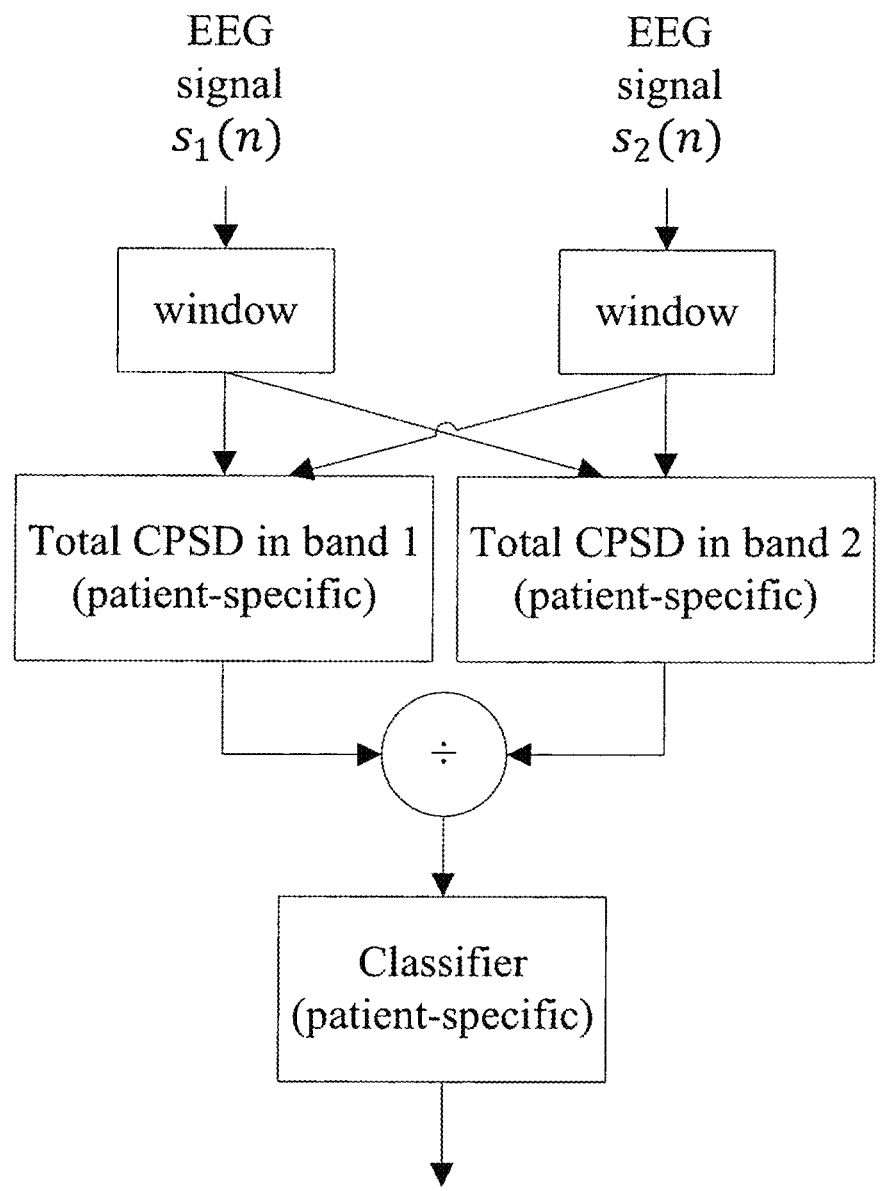
FIG. 8 illustrates the block diagram of the proposed seizure detection or prediction algorithm using a ratio of the band power in two bands of the CPSD.

This invention also describes methods for seizure detection and prediction using features computed from cross-power spectral density (CPSD) from two different electrodes. In one aspect of the invention, band power in a specific band of the CPSD may be used as a feature for seizure detection or prediction as shown in FIG. 7. In another aspect of this invention, ratios of CPSD in two bands can be used as features for seizure detection or prediction. FIG. 8 describes one embodiment of the invention where both band powers are computed from one CPSD. In another embodiment, band power from one CPSD may be divided from another band power from a different CPSD to obtain the ratio feature. The two different CPSDs may or may not share a common electrode. Such features have never been used before in the context of seizure detection or prediction.

Figure 9:
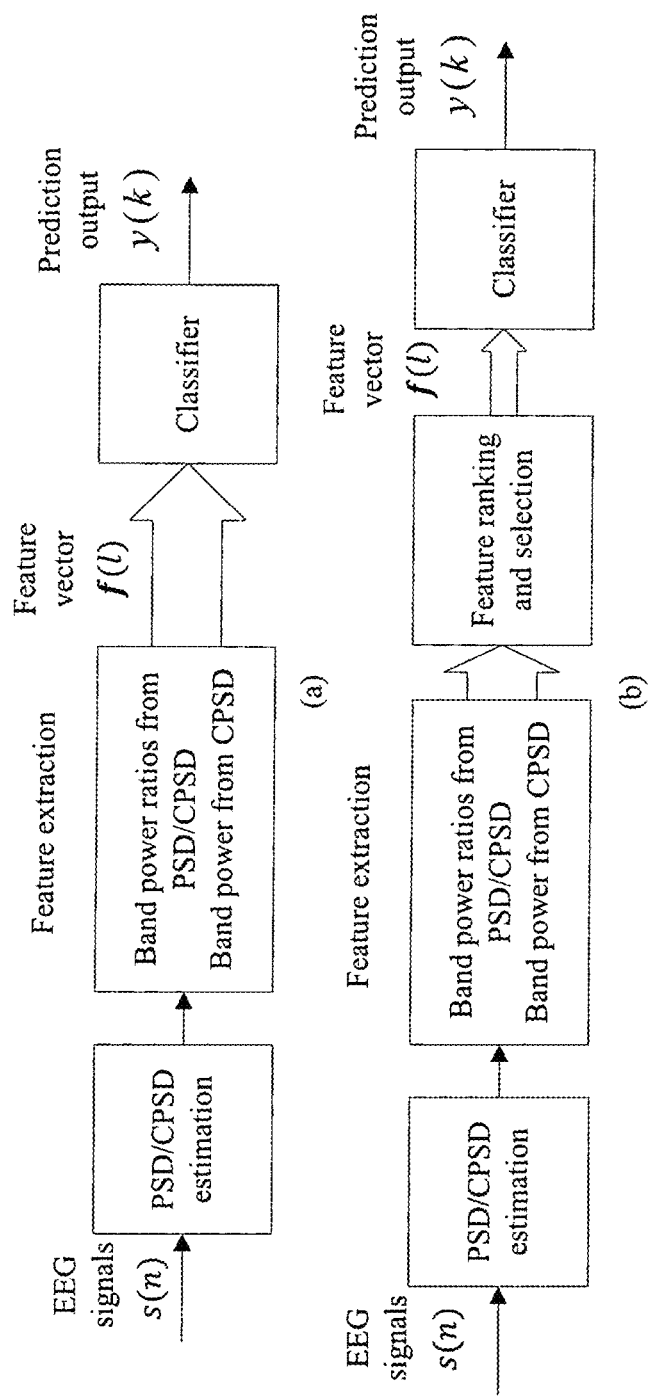
FIG. 9 illustrates the block diagrams of the proposed seizure detection or prediction algorithm (a) without feature ranking and selection and (b) with feature ranking and selection.

In one embodiment shown in FIG. 9(a), the proposed seizure detection or prediction method comprises 3 parts: (1) PSD/CPSD estimation, (2) feature extracter, (3) a classifier. In other embodiments, an optional postprocessing block can be applied to the decision variable of the classifier to remove noise and undesired fluctuations. Such post-processing block can be a Kalman filter, a median filter or a low pass filter. In another embodiment shown in FIG. 9(b), the seizure detection or prediction method comprises 4 parts: (1) PSD/CPSD estimation, (2) feature extracter, (3) feature selection and (4) a classifier, where features are ranked and selected to limit the number of features before they are input to the classifier.

Figure 10:
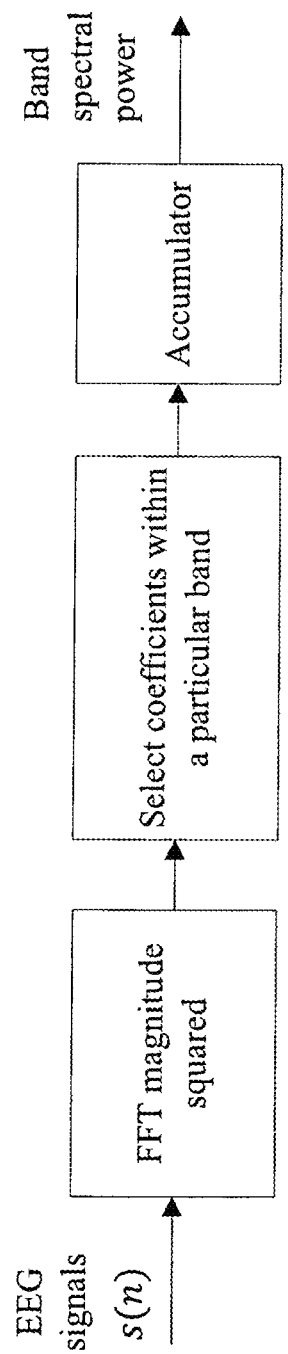
FIG. 10 illustrates the block diagram of a band spectral power computed using power spectral densities and retaining the power in a specific band.

In one embodiment shown in FIG. 10, in the first step, the input signal s(n) is windowed and the PSD of the windowed signal $s_l(n)$ is estimated, where l represent window index. These windows can be overlapping or non-overlapping. The PSD of any given signal s(n) describes the distribution of the signal's total average power over frequency. The ratio of spectral power can be computed in several ways. The spectral power of the windowed signal s(n) in a particular frequency band represents the power of the signal in that frequency band and is computed as the squared sum of the PSD values within that frequency band as shown in FIG. 10. In FIG. 10, the squares of magnitude of the power spectral density values corresponding to a particular band are accumulated to compute the band spectral power. Since power needs to be computed for each windowed segment $s_l(n)$, $P_i(l)$ is a time series whose l-th element represents the spectral power of the the input signal in the l-th window in band i and is defined as follows $$P_i(l) = \sum_{\omega \in band\ i} PSD_{s_l}(\omega)$$

In one embodiment, the rhythmic activity in an EEG signal sampled at 256 Hz is typically described in terms of the standard frequency bands: (1) β (3-8 Hz), (2) α (8-13 Hz), (3) β (13-30 Hz), (4) γ (30-128 Hz). In another embodiment, the γ band is further split into 5 sub-bands: (1) γ1 (30-47 Hz), (2) γ2 (53-70 Hz), (3) γ3 (70-90 Hz), (4) γ4 (90-97, 103-110 Hz), (5) γ5 (110-128 Hz). In this decomposition, power line is assumed to be at 50 Hz and its harmonics. In other embodiments, power line noise may exist at 60 Hz and its harmonics. The power at these frequency bands should be filtered out before features are extracted. In other embodiments, finer frequency bands can be used. These frequency bands can be overlapping or non-overlapping. Let $R_{i,j}(l)=P_i(l)/P_j(l)$ represent the ratio of spectral power in band i over that in band j in the l-th window. If the two band powers are computed from PSDs of two electrodes, the spectral power ratio is then computed as $R_{i,j}(l)=P_i(l)/Q_j(l)$, where P and Q represent the PSDs for two different electrodes. These ratios indicate the change of power distribution in frequency domain from interictal to preictal periods, which can be used to predict seizures.

In another embodiment, logarithm features can be used, where the logarithmic absolute spectral power is computed as $$P_i(l) = \log \sum_{\omega \in band\ i} PSD_{s_l}(\omega)$$

and the spectral power ratio is computed as $R_{i,j}(l)=P_i(l)-P_j(l)$. If the bands correspond to two different PSDs, then the spectral power ratio can be computed as $R_{i,j}(l)=P_i(l)-Q_j(l)$, where P and Q correspond to two different PSDs.

The band power in a CPSD can be computed using $$CP_i(l) = \sum_{\omega \in band\ i} CPSD(\omega)$$

where CPSD(ω) represents the distribution of cross power per unit frequency and is defined as the discrete time Fourier transform of the cross correlation sequence of two signals. The ratio of CPSD in two bands can be computed as $CR_{i,j}(l)=CP_i(l)/CP_j(l)$ where i and j correspond to different bands and l corresponds to the window index. In another embodiment, the cross-spectral band power ratio can be computed as $CR_{i,j}(l)=CP_i(l)/CQ_j(l)$ where CP and CQ correspond to two different CPSDs. In logarithmic domain, these ratios can be computed as $CR_{i,j}(l)=P_i(l)-CP_j(l)$ or $CR_{i,j}(l)=CP_i(l)-CQ_j(l)$.

Figure 11:
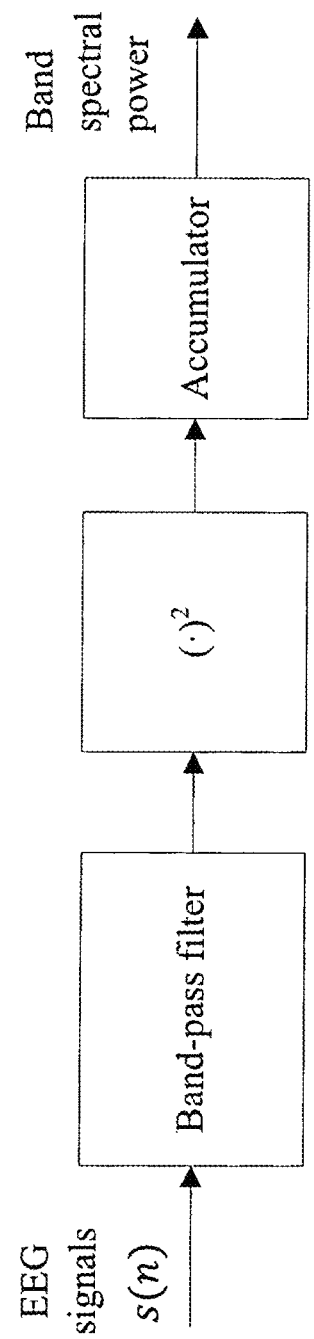
FIG. 11 illustrates the block diagram of a band spectral power computed using a band-pass filter and an accumulator.

In one embodiment, spectral power in a particular band can be computed by using a band-pass filter and an accumulator, whose system architecture is shown in FIG. 11.

In other embodiments, the ratio of spectral power could be computed from two different electrodes corresponding to either identical or different bands. Examples of these features are described in FIG. 5 and FIG. 6.

Postprocessing of a decision variable from a classifier is used to remove undesired fluctuations. In one embodiment, Kalman filter may be used. One example of Kalman filter is described in [Park Y, Luo L, Parhi K K, Netoff T. Seizure prediction with spectral power of EEG using cost-sensitive support vector machines. *Epilepsia*. 2011]. In other embodiments, low-pass filter or median filter can be used.

Electrode and Feature Selection

Selection of electrodes and features is carried out during the training phase of the classifier from EEG data of the specific subject. Once the feature and the classifier are trained, the system can be used during monitoring phase. Feature selection is important in limiting the number of the features input to a classifier in order to achieve a good classification performance and a less computationally complex classifier. Features can consist of the four proposed sets of features and may be combined with other known features. The four sets of proposed features include spectral power ratio, cross-channel spectral power ratio, absolute CPSD in certain bands and ratio of band power in CPSD. Other types of features may include PSDs in different bands, either in absolute or relative measure. Relative spectral power in a specific band is computed by normalizing the band PSD to the total PSD in the entire frequency range. In other embodiments, other features may be used. Features are ranked and selected in a patient-specific manner. A universal spectral power ratio such as δ-to-α ratio (DAR) has been explored in [Leon-Carrion J, Martin-Rodriguez J F, Damas-Lopez J, Barroso y Martin J M, Dominguez-Morales M R. Delta-alpha ratio correlates with level of recovery after neurorehabilitation in patients with acquired brain injury. *Clinical Neurophysiology*. 2009] and [Claassen J, Hirsch L J, Kreiter K T, Du E Y, Connolly E S, Emerson R G, Mayer SA. Quantitative continuous EEG for detecting delayed cerebral ischemia in patients with poor-grade subarachnoid hemorrhage. *Clinical Neurophysiol*. 2004] for seizure detection. However, this invention argues that ratio of spectral power in different bands has to be chosen in a patient-specific manner. One ratio that works well for one patient may not work well for another patient. The proposed invention describes methods to select specific ratio or ratios in a patient-specific manner.

Figure 12:
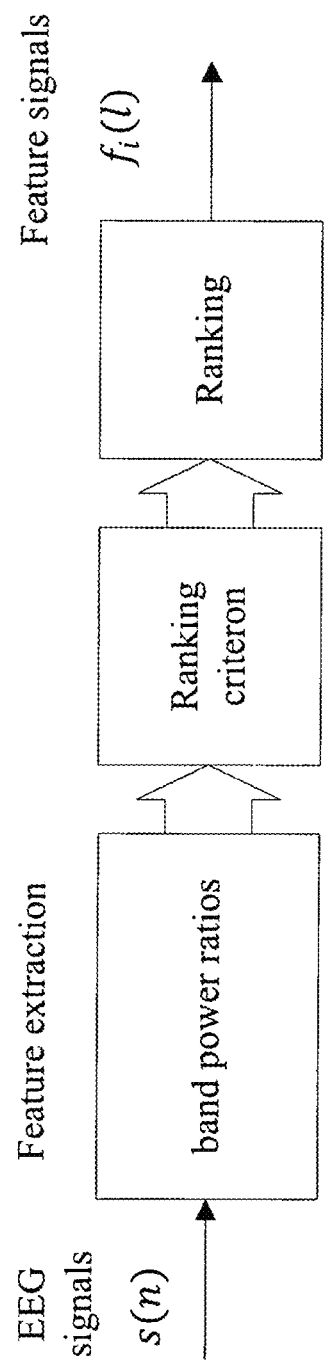
FIG. 12 illustrates the block diagram of the proposed feature ranking algorithm using band spectral power ratio features.

The importance of patient-specific feature ranking and selection is that spectral/cross-spectral power or spectral/cross-spectral power ratio that can be used as a good predictor or detector of seizures are very different for different patients. Therefore, features are first ranked and then one or more features are selected according to a predetermined criterion. In one embodiment of the ranking algorithm in FIG. 12, F-score can be used as the criterion for feature selection. F-score is a simple technique which measures the discrimination of two sets of real numbers. Given a training set $\{x_k, k=1, 2, \ldots, N\}$ which consists of N real numbers, and suppose that the number of samples from class one ($C_1$) and class two ($C_2$) are $N_1$ and $N_2$ ($N_1+N_2=N$), respectively, the F-score of this feature is defined as follows $$F = \frac{(\bar{x}_1 - \bar{x})^2 + (\bar{x}_2 - \bar{x})^2}{\frac{1}{N_1 - 1}\sum_{x_k \in C_1}(x_k - \bar{x}_1)^2 + \frac{1}{N_2 - 1}\sum_{x_k \in C_2}(x_k - \bar{x}_2)^2}$$

where $\bar{x}$, $\bar{x}_1$, $\bar{x}_2$ represent the mean of the features in the whole dataset, in the datasets belonging to $C_1$ and in the datasets belonging to $C_2$, respectively; and $x_k$ represents the k-th sample in the training set. In other embodiments, criteria such as correlation coefficient, mutual information, conditional entropy or p-value can be used.

Figure 13:
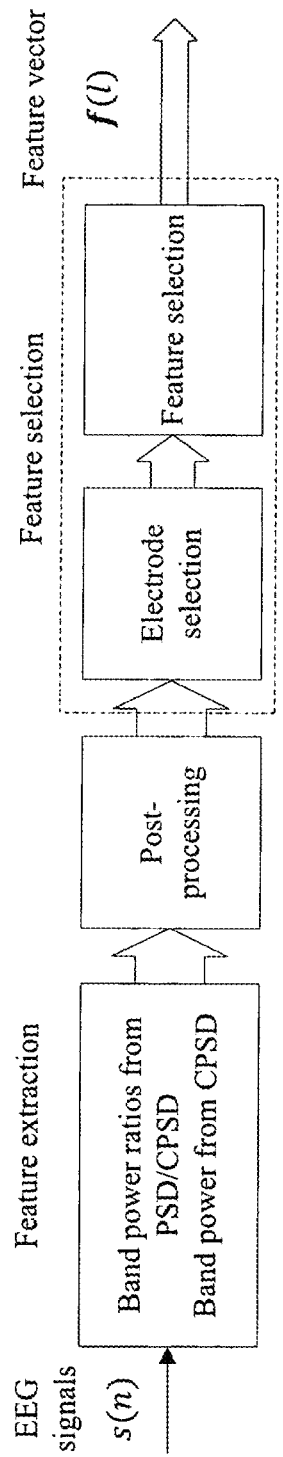
FIG. 13 illustrates the block diagram of the proposed multi-dimensional feature selection and ranking algorithm.

For patients where a single feature is not capable of achieving acceptable detection or prediction performance, multiple spectral powers or spectral power ratios may also be ranked and selected in a patient-specific manner. The multi-dimensional feature selection process is shown in FIG. 13, which includes electrode selection and feature selection.

Figure 14:
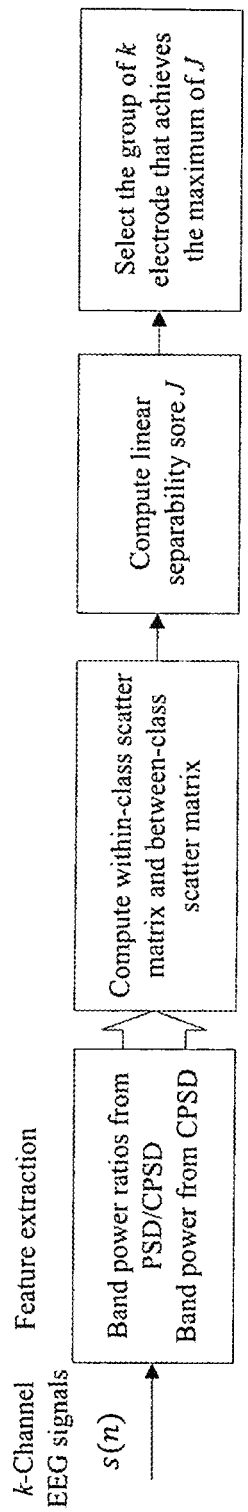
FIG. 14 illustrates the block diagram of the proposed electrode selection algorithm.

Electrode selection is first performed to limit the power consumed in sensing the signals from different locations of the brain. In one embodiment, electrodes can be selected according to a predetermined criterion. More specifically, the criteria for electrode selection can be described as selecting k electrodes such that features computed from the selected k electrodes achieve the maximum or minimum value of the predetermined criteria, where k represents the number of electrodes selected out of total electrodes, K. For example, if k=3 and K=16, all possible triplets of electrodes out of 16 electrodes are chosen for ranking. In other embodiments, linear separability is used as the predetermined criteria. Let $x=[x_1, x_2, \ldots, x_m]^T$ represents an m-dimensional feature vector. Define within-class scatter matrix ($S_\omega$) and between-class scatter matrix ($S_b$) as the following $$S_w = \sum_{i=1}^{i=c} p_i \sum_i$$

$$S_b = \sum_{i=1}^{i=c} p_i(\mu_i - \mu_0)(\mu_i - \mu_0)^T$$

where c represents the number of classes, $\Sigma_i = E[(x-\mu_i)(x-\mu_i)^T]$ represents the covariance matrix for class i, $p_i$ represents the probability of class i, $\mu_0$ represents the global mean vector, and $\mu_i$ represents the mean vector for class i, respectively. The criterion $$J(x) = \frac{|S_w + S_b|}{|S_w|}$$

takes large positive value when samples in the m-dimensional space are well clustered within each class, and the clusters of the different classes are well separated. FIG. 14 shows the block diagram of the electrode selection process using linear separability as the predetermined criteria. In other embodiment, electrodes can be selected without computing the features. For instance, electrodes where seizure originated (focus electrodes) can be selected to detect or predict seizures.

Figure 15:
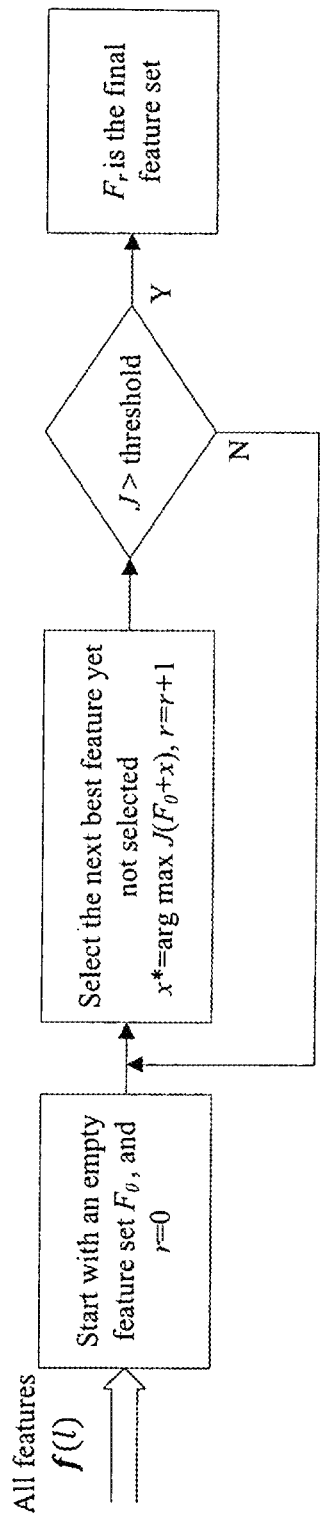
FIG. 15 illustrates the block diagram of the proposed sequential feature selection scheme.

Feature selection is then performed based on the features computed from the electrodes selected in the above step. In one embodiment, features are selected sequentially which can be described as starting from an empty feature set $F_0$, sequentially adding each of the features not yet selected such that the new feature combined with the selected features maximizes or minimizes a predetermined criteria. Such a feature selection scheme is illustrated in FIG. 15. In another embodiment, a set of features that achieves the maximum criterion is selected. In other embodiments, feature selection can be performed without electrode selection.

Examples of Discriminating Features

Figure 16:
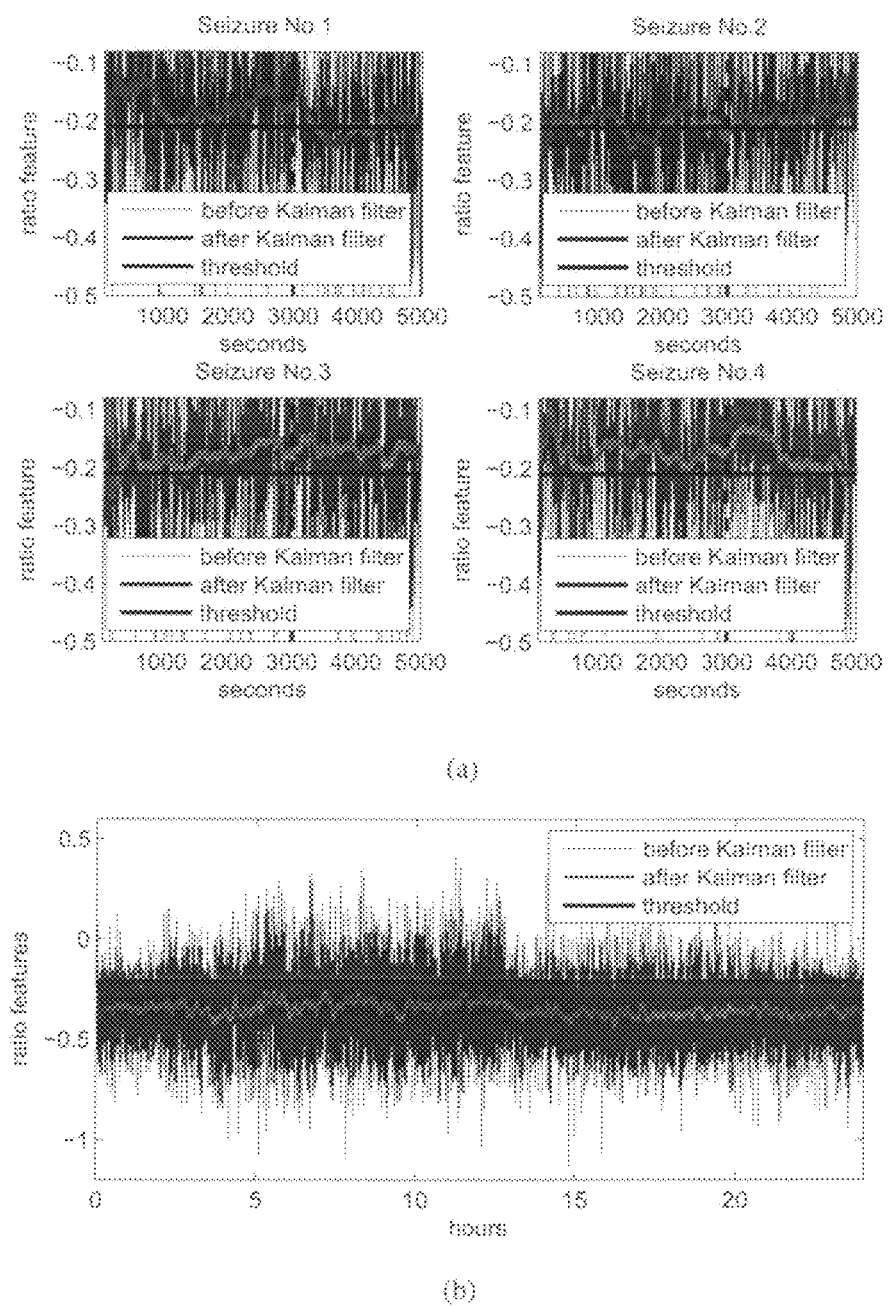
FIG. 16 illustrates the $\gamma5$-to-$\gamma4$ spectral power ratio of electrode No. 1 before and after postprocessing using the (a) ictal and (b) interictal intracranial EEG recordings of patient No. 1 in the Freiburg EEG database.
Figure 17:
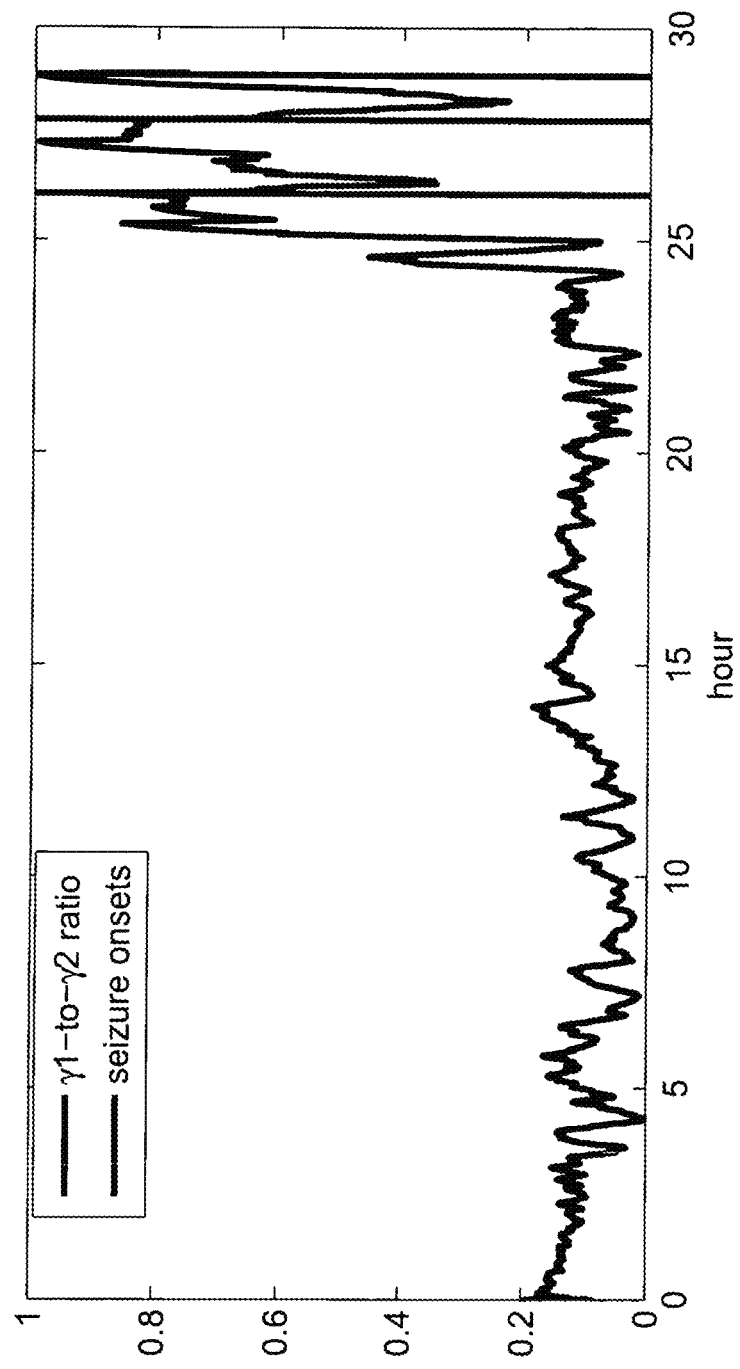
FIG. 17 illustrates the $\gamma1$-to-$\gamma2$ spectral power ratio of electrode No. 1 after postprocessing using scalp EEG recordings of patient No. 19 in the MIT Physionet database.

FIG. 16 illustrates the γ5-to-γ4 ratio of electrode No. 1 before and after postprocessing using the (a) ictal and (b) interictal recordings of patient No. 1 in the Freiburg EEG database, where the signals consisting of thin lines represent the feature signal before Kalman filtering, the signals consisting of thick lines represent the output of the Kalman filter, the horizontal lines represent the threshold, respectively. The signals in FIG. 16(a) correspond to four different seizures where each seizure onset occurs at exactly 3000 second time stamp. The signals in FIG. 16(b) correspond to interictal period of about 1 day duration. This particular ratio feature is shown to be a good seizure predictor for this particular patient as the feature always exceeds the threshold before seizure onset. FIG. 17 illustrates the γ1-to-γ2 ratio of electrode No. 1 after postprocessing using the EEG recordings of patient No. 19 in the MIT Physionet database, where the signal represents the ratio feature and the vertical lines represent seizure onsets, respectively. This ratio feature always increases significantly prior to the seizure onsets and stays at a low value during the interictal period. The two examples above show that discriminating features for seizure prediction for different patients are very different and therefore it is very important to find patient-specific features for each patient in order to achieve a good classification result.

Figure 18:
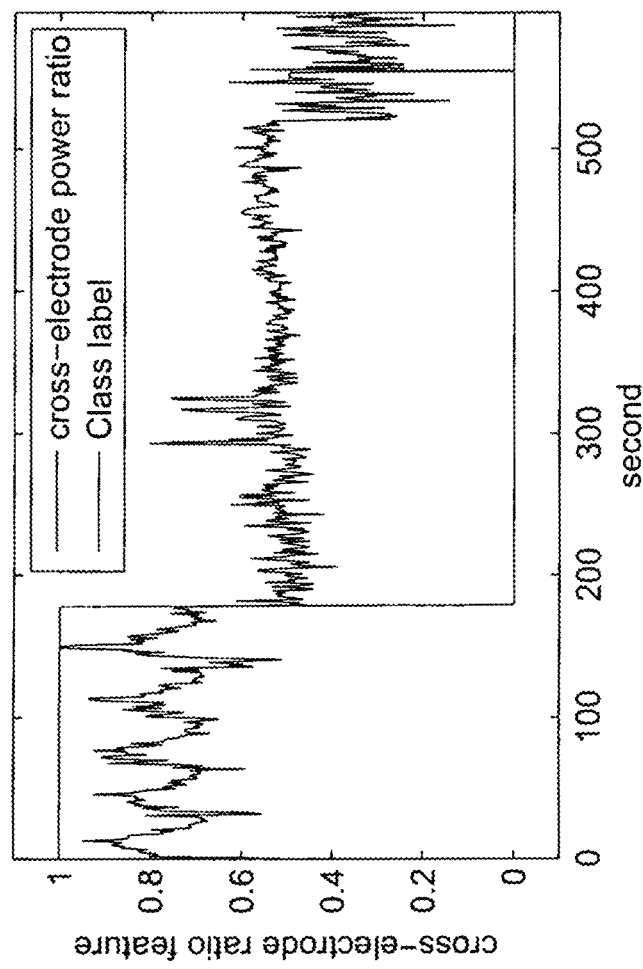
FIG. 18 illustrates the ratio of the spectral power in the frequency band of [170 Hz-200 Hz] from electrode No. 4 and the spectral power in the frequency band of [3 Hz-8 Hz] from electrode No. 8 using EEG recordings of dog No. 1 in the Upenn and Mayo Clinic's EEG dataset.
Figure 19:
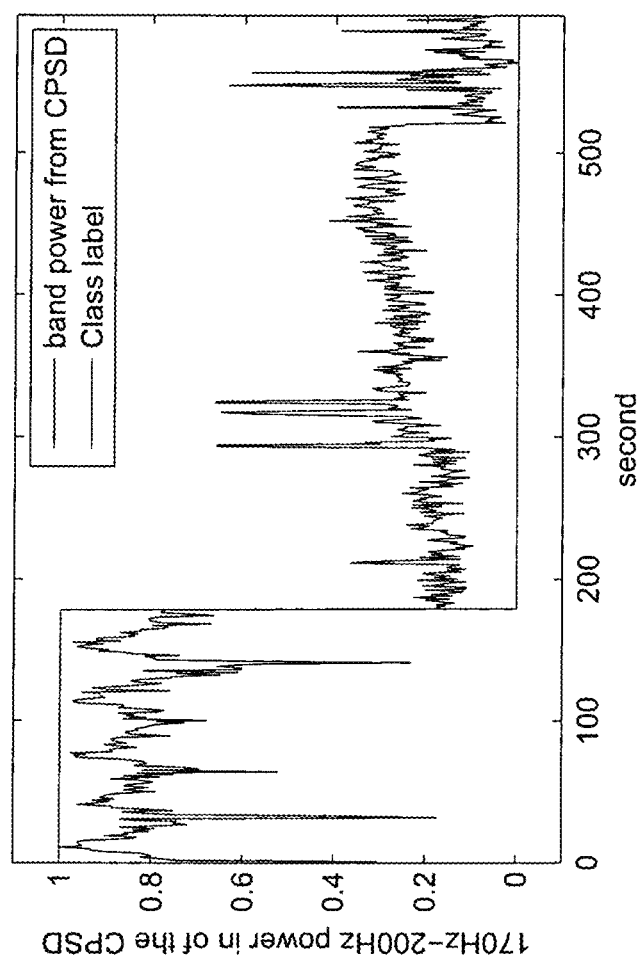
FIG. 19 illustrates the spectral power in the frequency band of [170 Hz-200 Hz] of the cross spectral power density of electrode No. 4 and electrode No. 8 using EEG recordings of dog No. 1 in the Upenn and Mayo Clinic's EEG dataset.
Figure 20:
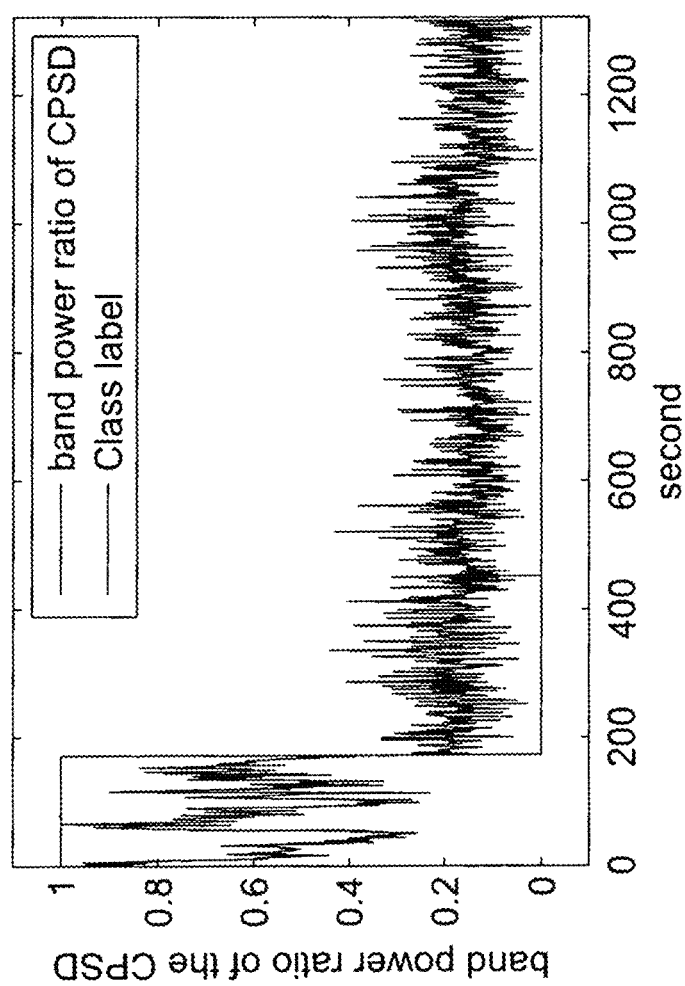
FIG. 20 illustrates the ratio of spectral powers in the frequency band of [3 Hz-8 Hz] and in the frequency band of [150 Hz-170 Hz] of the CPSD of electrode No. 15 and electrode No. 16 using EEG recordings of dog No. 2 in the Upenn and Mayo Clinic's EEG dataset.

It should noted that the proposed method is not restricted to spectral power ratio features from a single electrode only. In other embodiments, ratio of spectral powers in two bands from two electrodes can also be used as a good predictor or detector of seizures. FIG. 18 illustrates the ratio of the spectral power in the frequency band of [170 Hz-200 Hz] from electrode No. 4 and the spectral power in the frequency band of [3 Hz-8 Hz] from electrode No. 8 using EEG recordings of dog No. 1 in the Upenn and Mayo Clinic's EEG dataset as a feature for seizure detection, where the signal represents the ratio feature and vertical line separates the class label '1' from '0', i.e., ictal from interictal. In other embodiments, spectral power in a certain band or ratio of spectral powers in two different bands of the cross spectral power density (CPSD) of two electrodes can be used. FIG. 19 illustrates the spectral power in the frequency band of [170 Hz-200 Hz] of the CPSD of electrode No. 4 and electrode No. 8 using EEG recordings of dog No. 1 in the Upenn and Mayo Clinic's EEG dataset. FIG. 20 illustrates ratio of spectral powers in the frequency band of [3 Hz-8 Hz] and in the frequency band of [150 Hz-170 Hz] of the CPSD of electrode No. 15 and electrode No. 16 using EEG recordings of dog No. 2 in the Upenn and Mayo Clinic's EEG dataset, where the signal represents the ratio feature and vertical line separates the class label.

Figure 21:
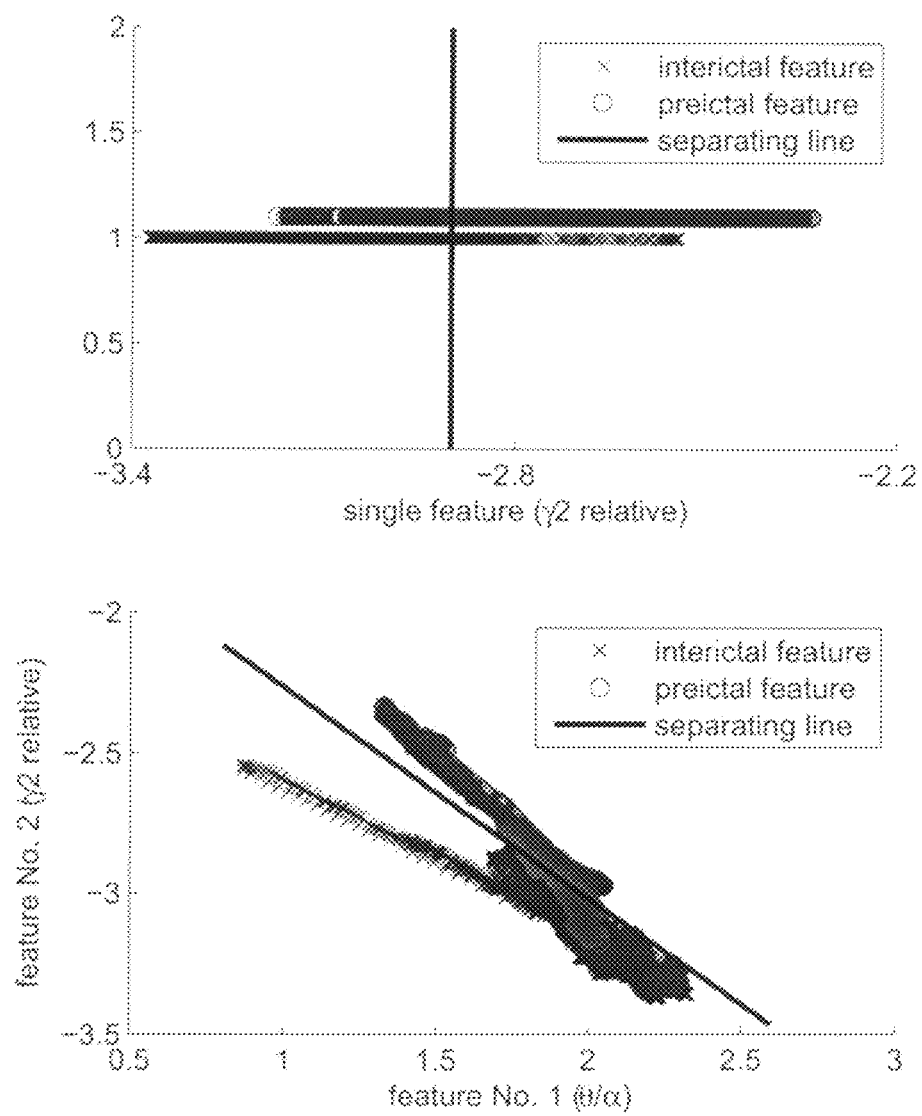
FIG. 21 illustrates the scatter plot of (a) a single $\gamma2$ spectral power and (b) a 2-dimensional feature of $\gamma2$ spectral power versus $\theta$-to-$\alpha$ spectral power ratio of electrode No. 2 using EEG recordings of patient No. 15 in the Freiburg database.

FIG. 21 illustrates the scatter plot of (a) a single γ2 spectral power and (b) a 2-dimensional feature of γ2 spectral power versus θ-to-α spectral power ratio of electrode No. 2 for patient No. 15 in the Freiburg database, where the cross points, circle points and the black line represent the interictal features, preictal features and separating line, respectively. While a single feature achieved a sensitivity of 80%, the 2-dimensional feature achieved a sensitivity of 100%.

Classifier Design

Figure 22:
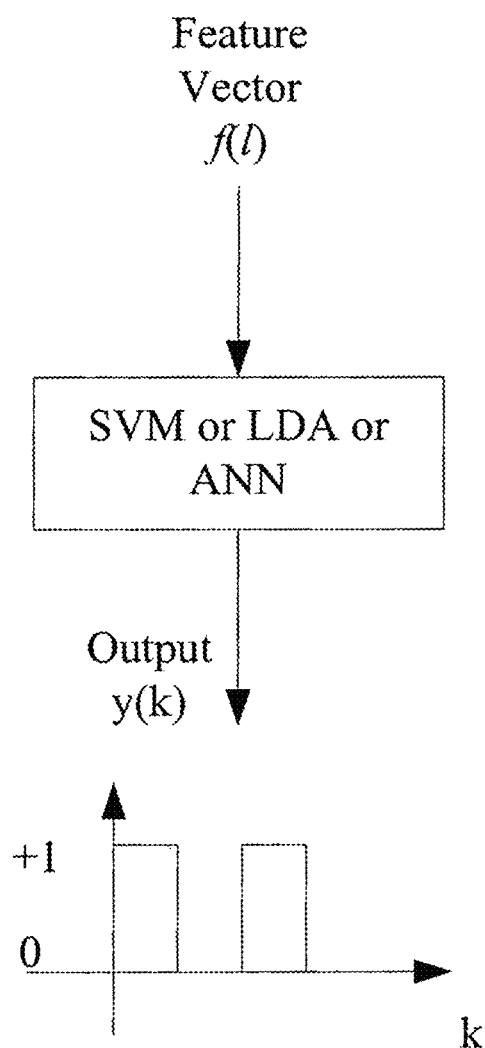
FIG. 22 illustrates the block diagram of a multi-variate classifier.

After feature extraction and selection, a classifier is trained to separate feature vectors in ictal period (or preictal period) from those in interictal period. A classifier can be a multi-variate classifier. In various embodiments, Support Vector Machine (SVM), Linear Discriminant Analysis (LDA), or Artificial Neural Network (ANN) classifiers can be used. In other embodiments, classifiers such Adaboost or random forrest can be used. This is illustrated in the block diagram shown in FIG. 22. The decision variable of the classifier can either be thresholded to get a binary decision or be processed to generate a probability for seizure activity.

In one embodiment, linear SVM is used in the classification step. In another embodiment, SVM with radial basis function kernel (RBF-SVM) is used. Consider a set of training data $\{x_i, y_i\}$ where $x_i$ is and input feature vector and $y_i \in \{-1, +1\}$ is the corresponding label. The final decision function of SVM is given by:

$$f(x) = \text{sign}\left(\sum_{n=1}^{N} \alpha_i y_i K(x_i, x) + b\right)$$

where x is the new feature vector, $\alpha_i$'s are the Lagrangian coefficients and b is the threshold. For linear SVM, $K(x_i, x) = x_i^T x$. For polynomial kernel SVM (with degree equal to p), $K(x, x_i) = (x_i^T x + 1)^p$. For RBF-SVM, $K(x_i, x) = \exp(-\|x - x_i\|^2 \sigma^2)$.

Figure 23:
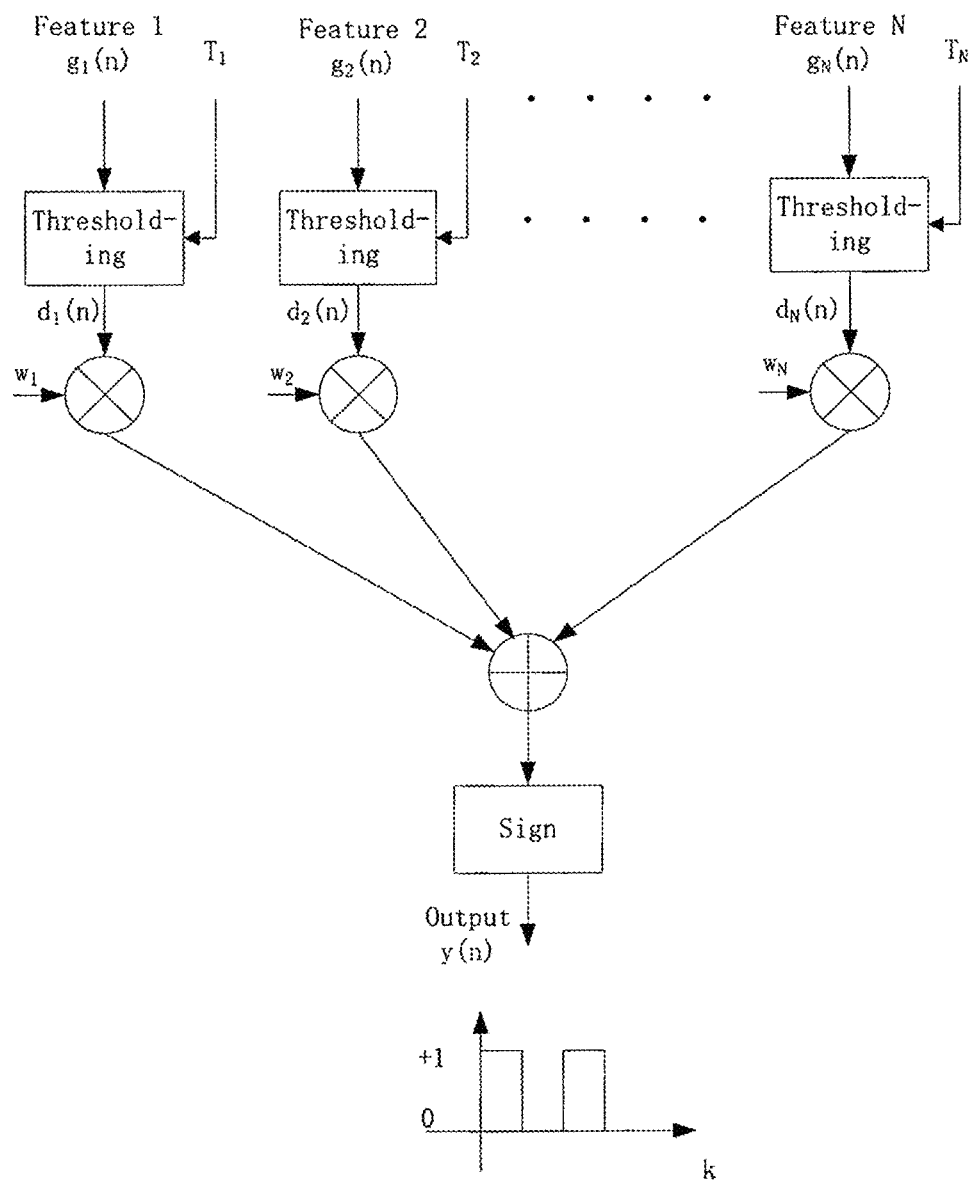
FIG. 23 illustrates the block diagram of an ADABOOST using decision stumps as basic learners.

A classifier can also consist of multiple univariate classifiers trained on a subset of features; the outputs of these classifiers can then be weighted and summed to compute a final output that is used to generate the final decision. In an embodiment, this said classification method is implemented as an ADABOOST classifier using decision stumps as basic learners. A block diagram of the ADABOOST classifier is shown in FIG. 23. This block diagram shows that N classifiers are combined to compute a decision variable. The features $g_i(n)$, $g_2(n)$, $g_N(n)$ are chosen from the feature set $f_1(n), f_2(n), \ldots, f_d(n)$. A feature $f_i(n)$ can map to one or many $g_k(n)$ features. The output of the thresholding block is denoted by $d_i(n)$ which is defined as:

$$d_i(n) = \begin{cases} -1 & g_i(n) < T_i \\ +1 & g_i(n) \geq T_i \end{cases} \quad (1)$$

where $T_i$ is a threshold parameter. The final output y(n) is given by:

$$y(n) = \text{sign}\left(\sum_{i=1}^{N} w_i d_i(n)\right) \quad (2)$$

where $\omega_i$ is the weight associated with the i-th classifier and $$\text{sign}(x) = \begin{cases} 0 & x < 0 \\ 1 & x \geq 0 \end{cases} \quad (3)$$

Figure 24:
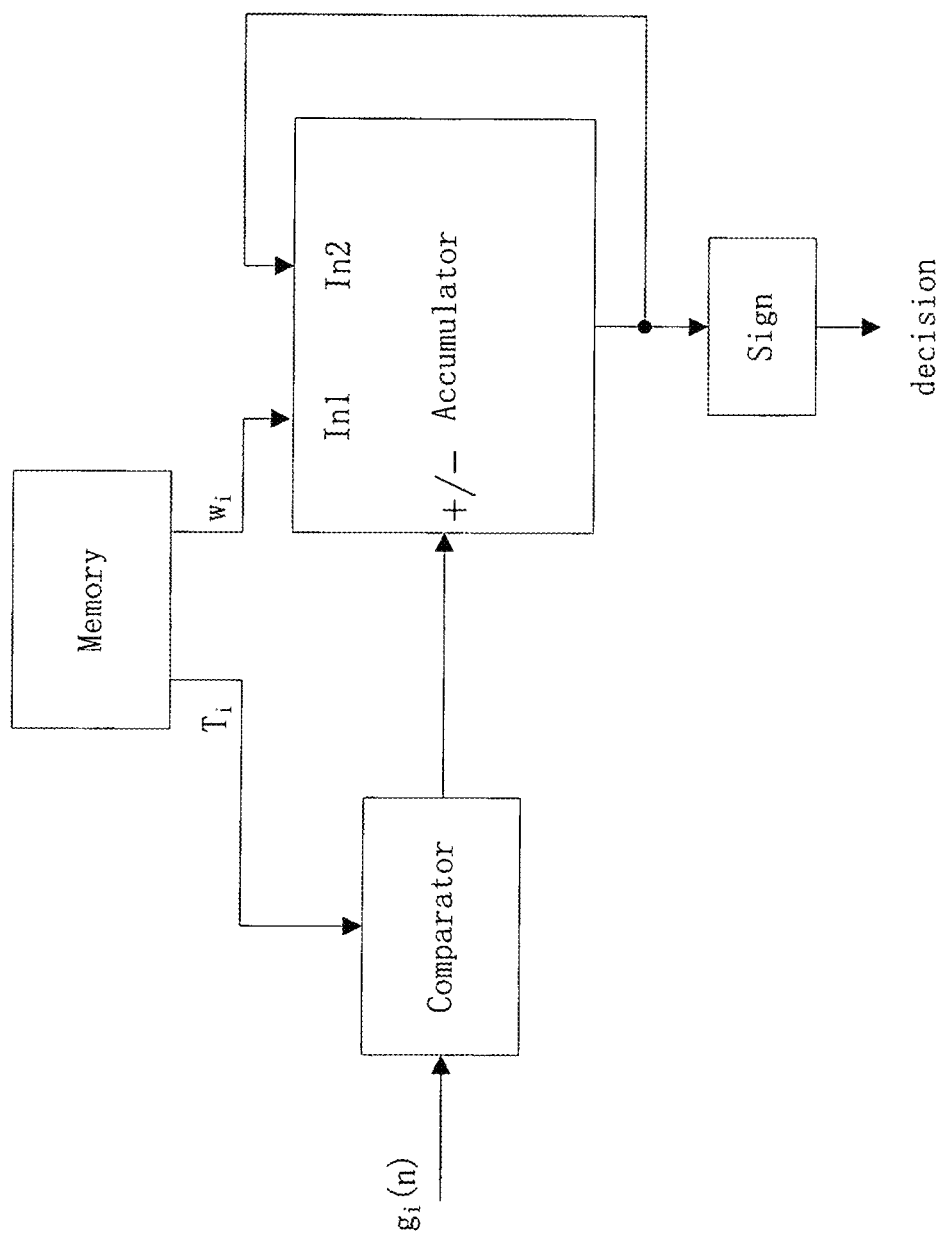
FIG. 24 illustrates an implementation of ADABOOST using serial processing.

An architecture that implements ADABOOST using sequential processing approach is shown in FIG. 24.

Device Design and Applications

Figure 25:
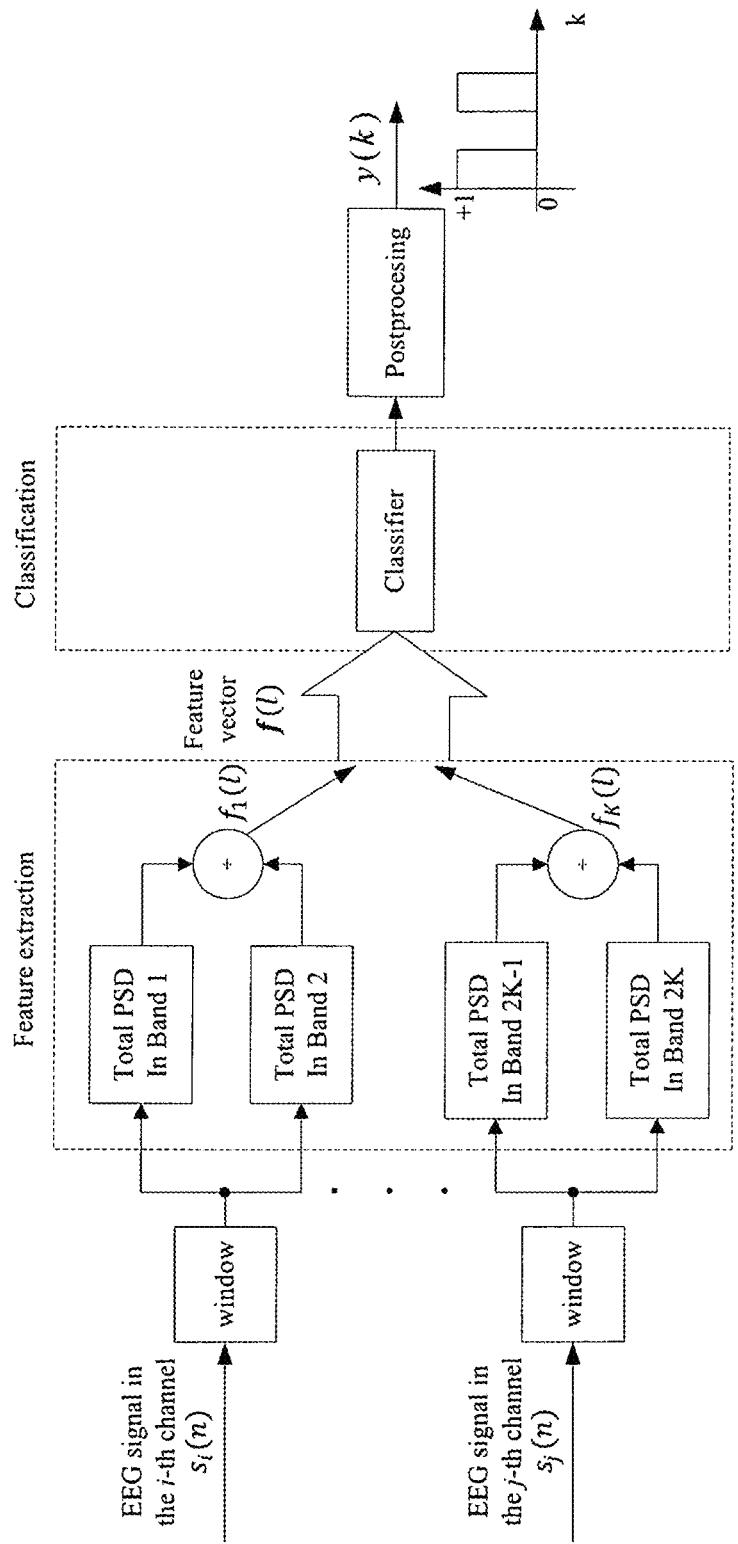
FIG. 25 illustrates the block diagram of an example of a hardware implementation of a seizure detection or prediction system.

In the final step, a seizure activity detector or predictor can be designed according to the selected electrodes, selected features and trained classifier. One example of a seizure activity detector in shown FIG. 25, where K band power ratios are used as features. In FIG. 25, $s_i(n)$ and $s_j(n)$ represent the EEG signal from the i-th and j-th electrode that have been selected, and $f_k(l)$'s represent the k-th spectral power or spectral power ratio feature of the input signal in the l-th window, respectively.

Figure 26:
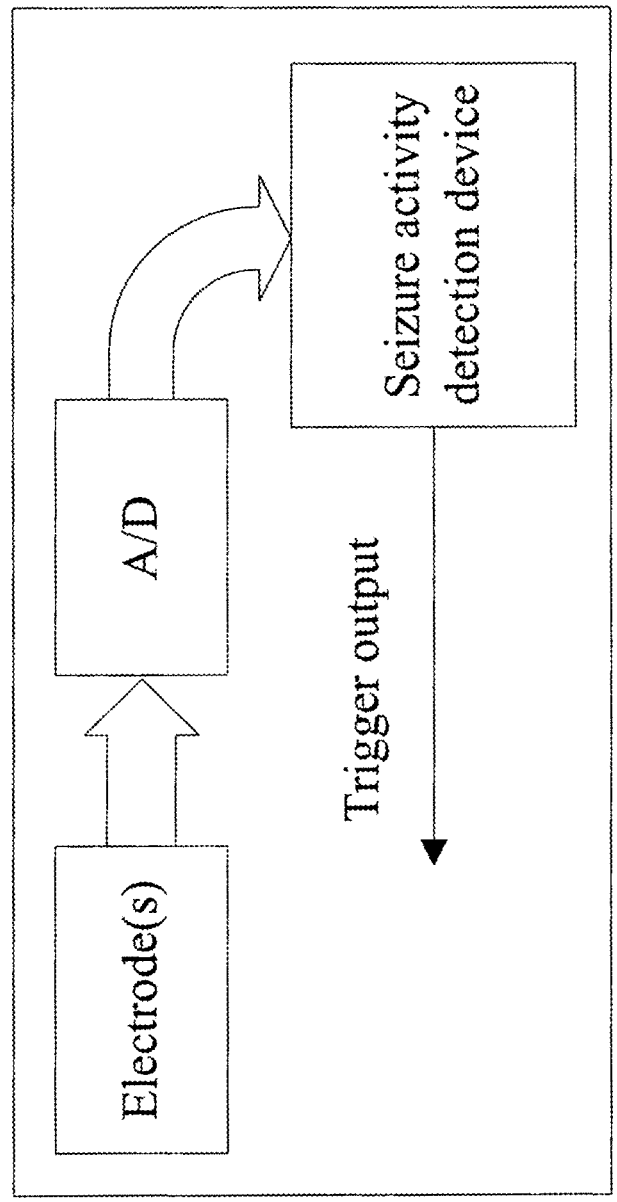
FIG. 26 illustrates a seizure activity detection device where one or more electrodes sense the EEG signals which are digitized using analog-to-digital converters (A/D), and then processed to create a seizure activity trigger signal.
Figure 27:
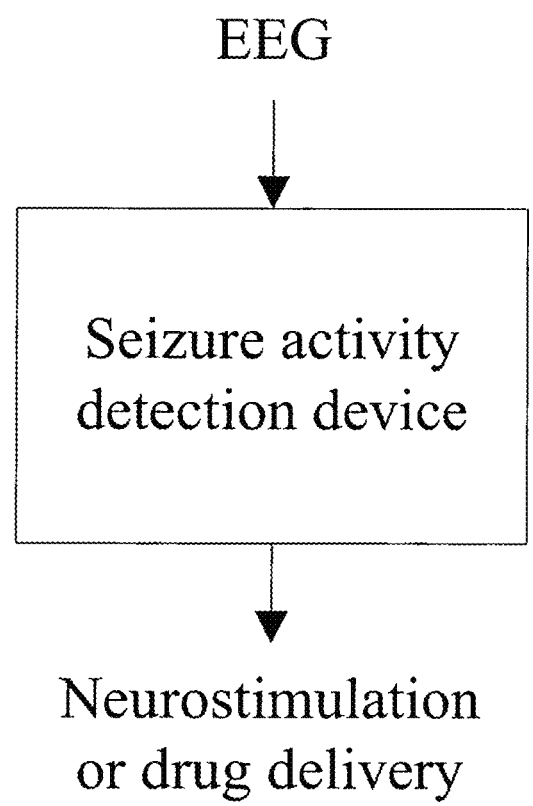
FIG. 27 illustrates a seizure detection device that creates a trigger signal from the input EEG signal(s) and the trigger signal activates neurostimulation or drug delivery.
Figure 28:
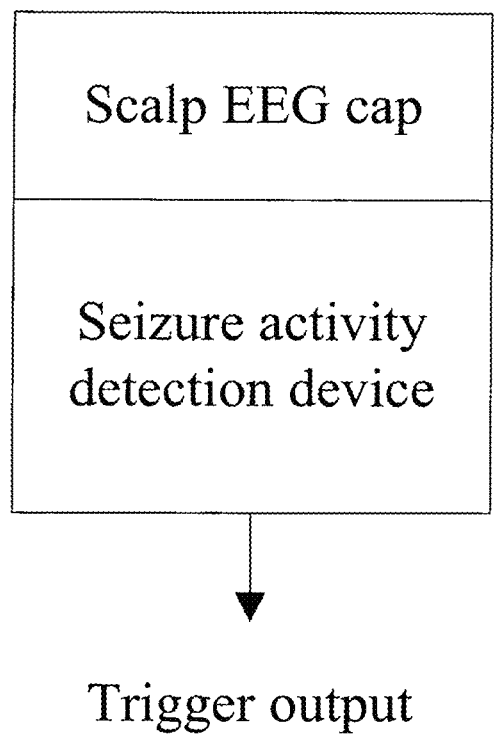
FIG. 28 illustrates a seizure detection device that process EEG signal(s) from scalp EEG and outputs a trigger signal to indicate onset of seizure activities.

A seizure activity detection device can be designed using the proposed method. Such a device can be implemented as shown in FIG. 26 where one or more electrodes sense the EEG signal. These signals are digitized using analog-to-digital converters (A/D), and then processed to create a seizure activity trigger signal. This trigger signal can be a binary warning signal to represent seizure detection or no detection. In another embodiment, the trigger signal may represent probability of seizure activity. In one application, this device can be implanted in the brain. In this application, the intracranial electrodes are processed to predict a seizure activity. The trigger signal then enables neurostimulation or delivery of an anti-epileptic drug (AED), which is illustrated in FIG. 27. In a wearable application shown in FIG. 28, the proposed device can process scalp EEG signals acquired from an EEG cap. A warning signal is generated to alarm the epileptic patient about a seizure onset.

The seizure activity detection device can be implemented using various implementation styles. In one embodiment, the device is implemented using an integrated circuit. In another embodiment, a field-programmable gate-array (FPGA) may be used. In yet another embodiment, the device may be implemented as a computer program containing a processor. Different applications impose different constraints. For example, in an implantable application, it is important to reduce power consumption such that the battery life lasts longer. In such an application, an integrated circuit realization is desired. In other applications, it may be useful to mark seizures in an unmarked EEG collected from a patient. This marking can be a first step in helping an epileptologist mark the seizures. In such an application, the marking significantly reduces the time of the epileptologist, as the markings only need to be corrected. In this application, the seizure activity detection device can be implemented as a computer program in a desktop computer or a laptop computer or an embedded device such as a computer tablet. In other applications, such as cloud computing and web server systems, the EEG can be uploaded to a web server where the seizure activity detection device is accessible by the web server.

For each patient, the performance of the proposed system is measured in terms of sensitivity and the false detection (or prediction) rate. Sensitivity, defined as $$\text{Sensitivity} = \frac{\text{\# of } TPs}{\text{\# of } TPs + \text{\# of } FNs} \quad (4)$$

measures the proportion of the ictal events in a patient that are correctly classified by the proposed algorithm, where TPs represents the true positives and FNs represents the false negatives.

In addition, the false positive rate (FPR) per hour demonstrates how many false alarms the proposed algorithm would generate in the interictal recordings. An approximately 30-min interval is considered as detection (or prediction) horizon. In other embodiment, other time interval may be considered.

For the Freiburg intracranial EEG database, the proposed algorithm achieves a high sensitivity of 100% and a FPR of 0.032 by using 1.167 electrodes and 2.78 features on average for seizure prediction. For the MIT scalp EEG database, the proposed algorithm achieves a sensitivity of 98.68% and a FPR of 0.0465 by using 1.29 electrodes and 5.05 features on average for seizure prediction.

CONCLUSION

Various embodiments of the present invention can be implemented using different selection of frequency bands, different ranking criteria, different postprocessing techniques and different types of the classifiers. These various embodiments can be implemented in implantable or wearable biomedical devices to trigger a signal when seizures are detected or predicted. This trigger signal can be used in a closed-loop therapy system to deliver anti-epileptic drugs or deliver a therapy based on electrical or magnetic stimulation or modulation of the brain. The stimulation could be delivered in an invasive or non-invasive manner.

It should be understood that these embodiments have been presented by way of example only, and not limitation. It will be understood by those skilled in the relevant art that various changes in form and details of the embodiments described may be made without departing from the spirit and scope of the present invention as defined in the claims. Thus, the breadth and scope of present invention should not be limited by any of the above-described exemplary embodiments, but should be defined only in accordance with the following claims and their equivalents.

What is claimed is:

1. An apparatus for monitoring and treating seizure activity from electroencephalogram, the apparatus comprising:
   a first electrode providing a first temporal signal and a second electrode providing a second temporal signal from a brain of a subject;
   a digital processing unit performing steps comprising:
      computing a cross-power spectral density for a band of frequencies using the first and second temporal signals;
      computing a second cross-power spectral density for a second band of frequencies;
      determining a ratio of the first cross-power spectral density to the second cross-power spectral density; and
      using the ratio to determine the seizure status of the subject; and
      in response to the seizure status of the subject, triggering delivery of a seizure treatment to the subject.

2. An apparatus for monitoring and treating seizure activity from electroencephalogram, the apparatus comprising:
   a first electrode providing a signal detected from a brain of a subject;
   a digital processing unit performing steps comprising:
      computation of a first spectral power in a first frequency band of the signal;
      computation of a second spectral power in a second frequency band of the signal;
      computation of a ratio of the first spectral power and the second spectral power;
      processing of the ratio for monitoring seizure activity of the subject; and
      in response to the seizure status of the subject, triggering delivery of a seizure treatment to the subject.

3. The apparatus in claim 2 wherein the first and second frequency bands are selected using a ranking algorithm during a training phase.

4. The apparatus in claim 2 further comprising using band-pass filters to compute the first spectral power and the second spectral power.

5. The apparatus in claim 2 further comprising using a fast Fourier transform to compute the first spectral power and the second spectral power.

6. The apparatus of claim 2 wherein the apparatus is within an implantable device.

7. The apparatus of claim 2 wherein the apparatus is within a wearable device.

8. An apparatus for monitoring and treating seizure activity from electroencephalogram, the apparatus comprising:
   a first electrode providing a first signal detected from a brain of a subject;
   electronic circuitry performing steps comprising:
      receiving the signal;
      determining a spectral power for a first frequency band of the signal;
      determining a spectral power for a second frequency band of the signal, the second frequency band different from the first frequency band;
      determining a ratio of the spectral power of the first frequency band to the spectral power of the second frequency band;
      applying the ratio to a classifier that uses the ratio to determine when a seizure is taking place;
      when a seizure is determined to be taking place, triggering delivery of a seizure treatment to the subject.

9. The apparatus of claim 8 wherein determining the spectral power for the first frequency band and determining the spectral power for the second frequency band comprises determining the spectral power for the first frequency band in a temporal window of signal and determining the spectral power for the second frequency band in the same temporal window of the signal.

10. The apparatus of claim 8 wherein the apparatus is within an implantable device.

11. The apparatus of claim 8 wherein the apparatus is within a wearable device.

* * * * *